United States Patent [19]
Durden, Jr. et al.

[11] 3,998,963
[45] Dec. 21, 1976

[54] TERTIARY BUTYL SUBSTITUTED CARBAMOYL OXIME PESTICIDES

[75] Inventors: John A. Durden, Jr., South Charleston; Anthony A. Sousa, Saint Albans, both of W. Va.

[73] Assignee: Union Carbide Corporation, New York, N.Y.

[22] Filed: May 21, 1975

[21] Appl. No.: 579,443

[52] U.S. Cl. .............................. 424/298; 424/300; 424/327
[51] Int. Cl.² .................. A01N 9/00; A01N 9/12
[58] Field of Search .................................... 424/298

[56] References Cited
UNITED STATES PATENTS 3,825,579   7/1974   Fujimoto et al. ............. 424/298 X

FOREIGN PATENTS OR APPLICATIONS 1,318,136   5/1973   United Kingdom

*Primary Examiner*—Jerome D. Goldberg
*Assistant Examiner*—Allen J. Robinson
*Attorney, Agent, or Firm*—Robert C. Brown

[57] ABSTRACT

O-[N-Methyl-N-[4-(t-butylphenyl)sulfenyl] carbamoyl] S-lower alkyl thiolacetohydroximate compounds exhibit outstanding activity for combating insects and mites and extremely low levels of toxicity to warm blooded creatures coupled with markedly reduced phytotoxicity as compared to closely related prior art compounds.

8 Claims, No Drawings

TERTIARY BUTYL SUBSTITUTED CARBAMOYL OXIME PESTICIDES

This invention relates to methods and compositions for combating insects and mites.

The compounds which are employed as the active ingredients in the pesticidal compositions of this invention are new compounds corresponding to the following general formula:

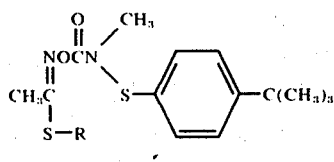

wherein R may be methyl, ethyl, or isopropyl.

These compositions are characterized by unexpectedly enhanced animal and plant safety together with remarkedly increased contact toxicity to insects.

Compounds similar to those described above are known and have been described in the literature. The known compounds heretofore described differ from the compositions described above primarily, in that the permissible substituents on the phenylsulfenyl moiety are halogen, nitro, lower alkoxy or lower alkyl. Plural substitution is also described. These compositions are described in U.S. Pat. Nos. 3,825,579, 3,856,972, and British Pat. No. 1,318,136. The pesticidal activity of the prior art compounds is essentially the same as the activity of the parent compounds, the parent compounds being those compounds in which the phenyl sulfenyl moiety on the carbamoyl nitrogen is replaced by hydrogen. In terms of mammalian toxicity the known phenylsufenyl compounds appear to exhibit a slight numerical advantage in mammalian toxicity when compared with their parent compounds on a weight basis. These differences in mammalian toxicity are slight and such differences as do exist appear to be within the limits of experimental accuracy. When the effective mammalian toxicity of the prior art compounds is compared with their parent compounds on the basis of molar weight ratios (this is believed to be a more accurate criterion for toxicity comparisons) it will be seen that the known phenylsulfenyl derivatives described in the prior art are actually more toxic to mammals than are their parent compounds. The only alkylphenylsulfenyl derivatives actually described in the prior art are the p-methylphenylsulfenyl derivatives which one would expect to exhibit the highest insecticidal activity due to the fact that pesticidal compositions including relatively large alkyl substituents are normally less effective than those having the smaller methyl groups. We have now found that the very specific class of 4-(t-butyl) phenylsulfenyl compounds described in the above given generic formula are dramatically superior to the phenylsulfenyl compounds of the prior art and to their parent compounds in terms of both pesticidal activity and reduced mammalian toxicity. The mammalian toxicity of the tertiary butylphenyl compounds of the present invention is reduced by a factor of 3 on both a molar weight and a pure weight comparison basis. These compounds also exhibit markedly diminished plant toxicity and a substantial enhancement of contact toxicity (relative to stomach toxicity) to insects as compared to the parent carbamates.

The preferred compound in accordance with this invention is O-[N-methyl-N-[4-(t-butylphenyl)sulfenyl] carbamoyl] S-methyl acetothiolhydroximate due to its extremely low mammalian toxicity and exceptionally high insecticidal activity against aphid, armyworm and bean beetle and its very low phytotoxicity against important economic crops. The second preferred compound according to this invention is O-[N-methyl-N-[4-(t-butylphenyl) sulfenyl] carbamoyl] S-isopropyl thiolacetohydroximate which also exhibits a very low level of mammalian toxicity; extremely low phytotoxicity; is an outstanding stomach poison against insects and also appears to be the most powerful contact poison for insects among all of the compositions tested.

The novel compositions of this invention can be prepared conveniently by reacting 4-t-butylbenzenesulfenyl halide with an appropriately substituted carbamoyl compound in accordance with the following general reaction scheme:

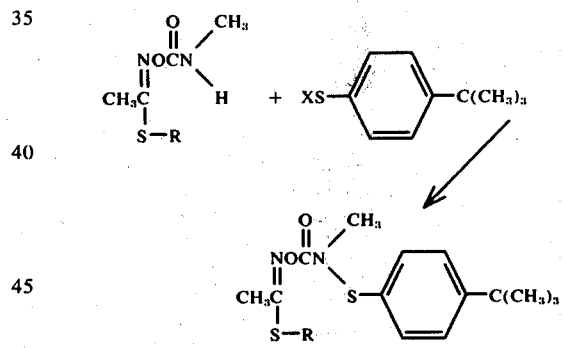

wherein R is as defined above and X is chlorine or bromine. The reaction is preferably conducted in the presence of an aprotic solvent and in the presence of a base such as a tertiary organic amine, preferably pyridine.

Alternatively, the novel compounds of this invention can also be prepared by the method illustrated in the following general reaction scheme:

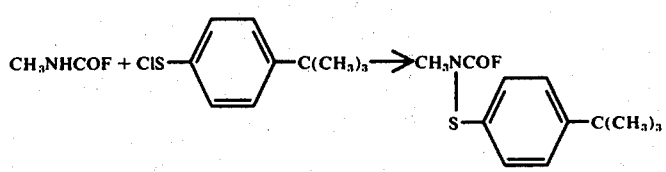

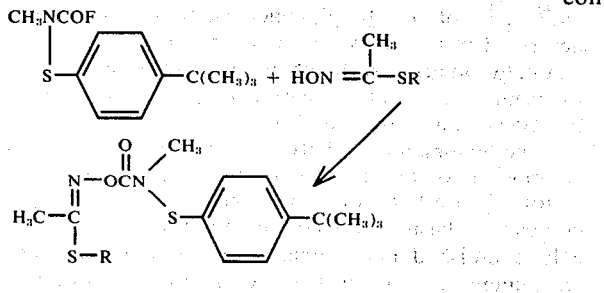

wherein R is as defined above. N-methyl carbamoyl fluoride used in reaction I can be prepared simply by the reaction of methyl isocyanate and hydrofluoric acid. Both reactions I and II are preferably conducted in the presence of an aprodic solvent in the presence of an acid acceptor, such as a tertiary amine, preferably pyridine.

The following specific examples are provided to more particularly illustrate the manner in which the novel compositions of this invention may be prepared.

EXAMPLE I

Preparation of O-[N-Methyl-N-[4-(t-butylphenyl)sulfenyl]carbamoyl] S-Methyl Acetothiolhydroximate.

To a mixture of 81 ml of dimethylformamide and 4.4 ml (0.056 mole) of pyridine was added 8.1 grams (0.05 mole) of O-(methylcarbamoyl) S-methyl acetothiolhydroximate. To this stirred solution was added dropwise with stirring grams (0.054 mole) 4-t-butylbenzene sulfenyl chloride over a one-minute period. After stirring 2 hours at ambient temperatures the mixture was added to one liter of cold water and stirred for 5 minutes. This mixture was extracted with ethyl ether and the ether extract as washed two times with water and, finally, dried over magnesium sulfate. The ether solution was filtered and the filtrate concentrated to produce a solid residue which, upon crystallization from 90/10 hexane/xylene gave 10 grams (61.2%) of product, O-[N-methyl-N-[4-t-butylphenyl)sulfenyl] carbamoyl] S-methyl acetothiolhydroximate m.p. 72°–74°.

Anal: Calc'd for $C_{15}H_{22}N_2O_2S_2$: C, 55.2; H, 6.8; N, 8.6. Found: C, 55.2; H, 6.7; N, 8.6.

EXAMPLE II

Preparation of O-[N-Methyl-N-[4-(t-Butylphenyl)sulfenyl]carbamoyl] S-Isopropyl Thiolacetohydroximate Following the procedure and using appropriate reactants in amounts similar to those in the Example I O-[N-methyl-N-[4-(t-butylphenyl)sulfenyl]carbamoyl] S-isopropyl thiolacetohydroximate was produced in 45 percent yield (8 grams), m.p. 77°–79°.

Anal.: Calc'd for $C_{17}H_{26}N_2O_2S_2$: C, 57.6; H, 7.4; N, 7.9. Found: C. 57.6; H, 7.2; N, 7.9.

Each of the new compounds were evaluated in comparison with known similar prior art compounds to determine their comparative pesticidal activity against mites and certain insects, including an aphid, caterpillar, a beetle and a fly. The new compounds were also tested for phytotoxicity on important economic crops including bean, corn, tomato and cotton. The new compounds were further evaluated for mammalian toxicity.

Suspensions of the test compouns were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°–70° F. and 50–70 per cent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100 –110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had peen previously ruled to facilitate counting. Temperature and humidity in the test room during the 24 hour holding period were 65°–70° F. and 50–70 per cent, respectively. Aphids which fell onto the paper and were unable to remain standing after being uprighted were considered dead. Aphids remaining on the plants were observed closely for movement and those which were unable to move the length of the body upon stimulation by prodding were considered dead. Per cent mortality was recorded for various concentration levels.

Southern Armyworm Leaf Spray Bait Test

Larvae of the southern armyworm (*Spodoptera eridania*, (Cram.)), reared on Tendergreen bean plants at a temperature of 80°±5° F. and a relative humidity of 50±5 per cent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for 3 days. Although the larvae could easily consume the whole leaf within 24 hours, no more food was added. Larvae which were unable to move the length of the body, even upon stimulation by prodding, were considered dead. Per cent mortality was recorded for various concentration levels.

Mexican Bean Beetle Leaf Spray Test

Fourth instar lavae of the Mexican bean beetle (*Epilachna varivestis*, Muls.), reared on Tendergreen bean plants at a temperature of 80°±5° F. and 50±5 per cent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test comound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F, for 3 days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.), reared according to the specifications of the Chemical Specialities Manufacturing Association (Blue Book, McNair-Dorland Co., N.Y. 1954; pages 243–244, 261) under controlled conditions of 80°±5° F. and 50±5 per cent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper covered surface. The test compounds were formulated by diluting the stock suspension with a 10 per cent (by weight) sugar solution to give a suspension containing 500 parts of test compound per million parts of final formulation, by weight. Ten milliliters of the test formulation were added to a souffle cup containing a 1-inch square of an absorbent cotton pad. This bait cup was introduced and centered on the blotting paper under the food strainer prior to admitting the anesthetized flies. The caged flies were allowed to feed on the bait for 24 hours, at a temperature of 80°±5° F. and the relative humidity of 50±5 per cent. Flies which showed no sign of movement on prodding were considered dead.

Mite Foliage Spray Test

Adults and nymphal stage of the two-spotted mite (*Tetranychus urticae* Koch), reared on Tendergreen bean plants at 80±5 per cent relative humidity, were the test organisms. Infested leaves from a stock culture were placed on the primary leaves of two bean plants 6 to 8 inches in height, growing in a 2½ inch clay pot. 150–200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5 per cent relative humidity for 6 days, after which a mortality count of motile forms was made. Microscopic examination for motile forms was made on the leaves of the test plants. Any individual which was capable of locomotion upon prodding was considered living.

Armyworm Immersion Test

The test organism used was the fourth instar larvae of the southern armyworm (*Spodoptera eridania*, (Cram.)) reared on Tendergreen beans in a room where temperature was held at 80° ± 5° F. and relaitve humidity 50 ± 5 percent.

Ten randomly selected larvae were thoroughly wetted in a formulated mixture of the chemical (50 ml) by pouring the insects and formulation from one beaker to another six times. Excess liquid was removed by transferring the larvae to paper towels. An equivalent amount of a water solution containing acetone and emulsifier in the same concentrations as the insecticidal mixture but without the candidate insecticide was applied in the same manner as a controls for the experiment. When dry, 5 larvae were placed in each of two 9-cm Petri dishes lined with filter paper and containing one fully expanded Tendergreen bean leaf per dish as food.

The closed dishes were held at 80°–85° F. for 3 days. Although the larvae can easily consume the whole leaf within 24 hours, no more food was added. Check larvae remained vigorous during the entire holding period. At the end of the holding period larvae which were unable to move the length of the body, even upon stimulation, were considered dead.

Fly Immersion Test

The test organisms used were 4 to 6 day old adult houseflies (*Musca domestica*, L.) reared under controlled conditions of 80° + 5° F. and 50 + 5 percent relative humidity. The adult flies were immobilized by anesthetizing with $CO_2$. Twenty-five immobilized individuals (males and females) were then used for the test of each test compound.

Twenty-five randomly selected adult flies were thoroughly wetted in a formulated mixture of the test chemical (50 ml) by pouring the insects and formulation from one beaker to another six times. Excess liquid was removed by transferring the insects into a standard food strainer (5-inch diameter) which was then blotted with a paper towel. The treated flies were transferred to clean food strainer which was inverted over a paper cup containing a wad of cotton saturated with a 10 percent aqueous sugar solution provided as food for surviving insects. An equivalent amount of a water solution containing acetone and emulsifier in the same concentrations as the insecticidal mixture but without the candidate insecticide was applied to other flies in the same manner. These insects serve as controls for the experiment.

The surviving caged flies were allowed to feed on the sugar water for a period of 24 hours. Room temperature and humidity are 80° + 5° F. and 50 + 5 percent relative humidity, respectively. At the end of the holding period flies which show no sign of movement upon stimulation were considered dead.

Phytotoxicity Test

Experiments were also conducted to determine the phytotoxicity of representative compositions with respect to healthy fresh plants. Solutions of the compounds were prepared as described above to provide a concentration of 2500 parts per million of the test compound. The test plants were sprayed in accordance with the procedure described above for the Mite Foliage Spray Test so as to deliver approximately 100 milliliters of test solution to the leaves of each plant tested. The sprayed plants and controls were set aside for approximately one hour to allow the foliage to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured.

Mammalian Toxicity

These compositions were also evaluated to determine their peroral toxicity to mammals by conventional methods. The animal selected for this experiment was the rat. The test results obtained are expressed in terms of the number of milligrams of composition per kilogram of weight of the animal required to achieve a mortality rate of 50 percent ($LD_{50}$).

The results of these experiments are summarized and set forth in Tables 1 and 2 below.

Compounds 1, 2 and 3 in the tables are the parent N-methyl carbamate compound of the new compounds of this invention. Compound 1 is known by the generic name methomyl and is a well known and widely used commercial pesticide. Compounds 4 to 7 are the variously substituted phenyl sulfenyl derivatives of the parent compounds which have also previously been described in the literature. Compounds 8, 9 and 10 are 4(t-butyl)phenyl sulfenyl derivatives of this invention. Compounds 8 and 9 are the preferred species according to this invention, due to their overall dramatically superior biological properties.

In Table 1 are presented insect and rat toxicity data (bait tests) on a comparative basis of the compounds described above. Although insect toxicity is frequently reported in ppm required for a 50% kill ($LD_{50}$), and these data are presented in Table 1 a more accurate comparison of relative toxicity is reflected by molar weight $LD_{50}$ values ($LD_{50}$ ppm)/mole. wt.). Rat toxicity is also more meaningfully compared on the basis of molar weight $LD_{50}$ values. The relative efficacy of the parent compounds as compared to the previously known derivatives and as compared to the new compounds of this invention is also shown in Table 1. The ratio of efficacy as contact poisons (immersion/bait) of the compounds tested against Armyworm and House Fly is presented in Table 2 along with the results of the phytotoxicity tests of the compounds on bean, corn, tomato and cotton.

TABLE I

Insect $LD_{50}$ (ppm) [a] (b)

$$\begin{array}{c} O \\ \parallel \\ CH_3C \end{array} \begin{array}{c} \diagdown \\ \diagup \end{array} C \begin{array}{c} \diagup NOCN \\ \diagdown SR' \end{array} \begin{array}{c} CH_3 \\ \diagdown R \end{array}$$

| Compound No. | R | R' | Aphid | Mite | Armyworm | Bean Beetle | Housefly | Rat $LD_{50}$ mg/Kg [a] (b) |
|---|---|---|---|---|---|---|---|---|
| 1 | H | $CH_3$ | 4 | 500 | 11[0.068] (−) | 70 | 4[0.02] (−) | 48.5[0.33] (−) |
| 2 | " | $CH(CH_3)_2$ | 25 | 450 | 17[0.089] (−) | 30 | 11[0.06] (−) | 7.7[0.04] (−) |
| 3 | " | $CH_2CH_3$ | 12 | 250 | 11[0.062] (−) | 38 | 3 | |
| 4 | 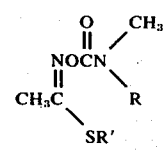 | $CH_3$ | 2 | 500 | 10[0.033] (2.1) | 70 | 8 | 65[0.21] (1.43) |
| 5 | 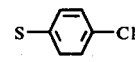 | $CH(CH_3)_2$ | 3 | 58 | 30[0.09] (1.0) | 50 | 50[0.15] (0.4) | 16.2[0.048] (0.83) |
| 6 | 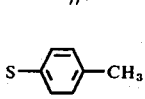 | $CH_3$ | 5 | 95 | 6[0.021] (3.2) | 15 | 2 | 56.6[0.2] (1.5) |

TABLE I-continued

Insect $LD_{50}$ (ppm) [a] (b)

$$\begin{array}{c} O \quad CH_3 \\ \| \quad / \\ NOCN \\ \| \quad \backslash \\ CH_3C \quad R \\ \backslash \\ SR' \end{array}$$

| Compound No. | R | R' | Aphid | Mite | Armyworm | Bean Beetle | Housefly | Rat $LD_{50}$ mg/Kg [a] (b) |
|---|---|---|---|---|---|---|---|---|
| 7 | " | $CH(CH_3)_2$ | 5 | 42 | 12[0.038] (2.3) | 15 | 50[0.16] (0.38) | 18.7[0.06] (0.67) |
| 8 | $S-\phi-C(CH_3)_3$ | $CH_3$ | 2.5 | 380 | 4[0.012] (5.7) | 20 | 17[0.05] (0.4) | 196[0.6] (0.5) |
| 9 | " | $CH(CH_3)_2$ | 9 | 42 | 19[0.054] (1.6) | 30 | 50[0.143] (0.43) | 71.3[0.2] (0.2) |
| 10 | " | $CH_2CH_3$ | 5 | >500 | 14[0.041] (1.52) | 20 | 13 | — | a. $LD_{50}$ ppm/mole wt.

b. $\dfrac{(LD_{50} \text{ ppm/mole wt.}) \text{ parent}}{(LD_{50} \text{ ppm/mole wt.}) \text{ derivative}}$

TABLE II $$\begin{array}{c} O \quad CH_3 \\ \| \quad / \\ NOCN \\ \| \quad \backslash \\ CH_3C \quad R \\ \backslash \\ S-R' \end{array}$$

| Compound No. | R | R' | Toxicities - Imm $LD_{50}$ ppm | | Rat Tox. $LD_{50}$(mg/kg) | Phytotoxicity[a] | | | |
|---|---|---|---|---|---|---|---|---|---|
| | | | Armyworm | Housefly | | Bean | Corn | Tomato | Cotton |
| 1 | H | $CH_3$ | 8(2)[b] | 32(8) | 48.5 | BuCl 2 | 1 | Bu 2 | *Bu 3 |
| 2 | H | $CH(CH_3)_2$ | 53(3.1) | 66(6) | 7.7 | Bu 2 | Bu 2 | Bu 2 | Bu 2 |
| 3 | H | $CH_2CH_3$ | — | — | 17.7 | 2 | 1 | 2 | 2 |
| 4 | $S-\phi-Cl$ | $CH_3$ | 47(0.47) | 24(3) | 65 | Trif. 3 | 1 | fmn 2 | *Bu 3 |
| 5 | $S-\phi-Cl$ | $CH(CH_3)_2$ | 4.5(0.15) | 25(0.5) | 16.2 | Trif. 3 | 1 | fmn 2 | Bu 2 |
| 6 | $S-\phi-CH_3$ | $CH_3$ | 10(1.7) | 14(7) | 56.6 | 1 | 1 | 1 | Bu 2 |
| 7 | $S-\phi-CH_3$ | $CH(CH_3)_2$ | 14.4(1.2) | 25(0.5) | 16.2 | 1 | 1 | 1 | 1 |
| 8 | $S-\phi-C(CH_3)_3$ | $CH_3$ | 4(1) | 14(0.8) | 196 | 1 | 1 | 1 | Bu 2 |
| 9 | $S-\phi-C(CH_3)_3$ | $CH(CH_3)_2$ | 5(0.25) | 10(0.2) | 71.3 | 1 | 1 | 1 | 1 |
| 10 | $S-\phi-C(CH_3)_3$ | $CH_2CH_3$ | — | — | — | 1 | 1 | 1 | 1 |

[a] ratings 1 thru 5 where "1" is no effect and "5" is complete destruction.
[b] (Imm/Bait)
Bu - leaf burn
fmn - formative
Cl - chlorosis
Trif. - trifoliate effect.
* - stunting Examination of the data presented in Tables I and II confirm the maintenance of insect toxicity of the previously known arylsulfenyl derivatives at levels generally comparable to those of the parent compounds and even in some cases demonstrating slight improvements. However, the safety effect of these previously known derivatives in terms of mammalian toxicity is not consistent. Note that the rat $LD_{50}$ of the parent compound methomyl) is 0.33 moles while the rat $LD_{50}$ of the known arylsulfenyl derivative (compound 6) is 0.2 moles, indicating that the 4-methylphenyl sulfenyl derivative is at least 50 percent more toxic to mammals than is the parent compound. Compound 4 indicates a similar increase in mammalian toxicity as compared to its parent, compound 1. These results are to be contrasted with the mammalian toxicity results exhibited by the novel t-butyl phenyl sulfenyl derivatives of this invention. Novel compound 8 had a rat $LD_{50}$ of 0.6 moles as compared to 0.33 for the parent compound and as such is about twice as safe as the parent. When compared on a weight basis, compound 8 is at least 4 times less toxic to mammals than its parent compound. At the same time it should be observed compound 8 exhibits a dramatic improvement in toxicity against all insects tested with the exception of house fly, which is not an economically important crop pest. Compound 9, as compared to is parent compound, also demonstrates dramatic improvement in activity against all insect species, again with the exception of house fly, together with a substantial reduction in mammalian toxicity.

Mammalian and insect toxicity obviously are critical factors in determining the ultimate utility of agricultural insecticides. Equally important however is the toxicity of the material to crop plants where insect infestations are found. Parent compound 1 (methomyl), a widely used commercial agricultural pesticide and parent compound 2 are both phytotoxic to one or more of the crop plants shown in Table 2. In fact, the phyotoxicity of compound 1 (methomyl) to cotton is so great as to significantly curtail the use of this otherwise highly desirable pesticide on cotton. All but one of the known phenyl sulfenyl derivatives of the parent compounds exhibit moderate to severe phytotoxicity toward one or more of these important economic crops. Except for the moderate leaf burn injury of compound 8 on cotton, all of the novel compositions of this invention exhibit no phytotoxic effect whatever against bean, corn, tomato or cotton. This is a highly significant characteristic and one which profoundly influences the ultimate utility of the claimed compounds as agricultural pesticides.

A more subtle but nonetheless very important property affecting the ultimate utility of insecticidal compositions is the relative efficiency of the material as a body contact toxicant as opposed to a stomach poison. In the case of agricultural insecticides, toxicity by body wall penetration may in fact be more important than is toxicity resulting from ingestion. Thus it is important to observe that compounds 1 and 2 are significantly more toxic as stomach poisons than as contact poisons to both army worm and house fly. New compound 8 is an outstanding contact poison to army worm and to house fly while compound 9 also possesses dramatically superior contact poison characteristics.

The new compounds of this invention, especially compounds 8 and 9 are unique among this entire class of compounds in their significantly superior biological properties in all of the characteristics which determine the ultimate utility of agricultural pesticides.

It will be understood that the insect species employed in the above test are merely representative of a wide variety of pests that can be controlled by use of the novel compounds of this invention.

The compounds contemplated in this invention may be applied as insecticides and miticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant after it is applied to the plant and wash it off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 per cent by weight. Satisfactory sprays, dusts, or granules for general use contain from about ¼ to 15 pounds of active toxicant per acre.

The pesticides contemplated herein prevent attack by insects and mites upon plants or other material to which the pesticides are applied. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are compatible with other constituents of the spray schedule, and they may be used in the soil; upon the seed, or the roots of plants without injuring either the seeds or roots of plants.

What is claimed is:

1. An insecticide and miticide composition comprising an insecticidally and miticidally effective amount of a compound of the formula:

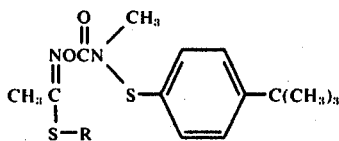

wherein R is methyl, ethyl or isopropyl and an acceptable carrier compound.

2. The composition according to claim 1 wherein R of said compound is methyl.

3. The composition according to claim 1 wherein R of said compound is ethyl.

4. The composition according to claim 1 wherein R of said compound is isopropyl.

5. A method of controlling insect and mite pests which comprises subjecting them to a lethal amount of a compound of the formula:

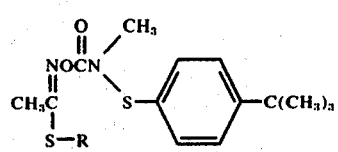

wherein R is methyl, ethyl or isopropyl.

6. The method according to claim 5 wherein R of said compound is methyl.

7. The method according to claim 5 wherein R of said compound is ethyl.

8. The method according to claim 5 wherein R of said compound is isopropyl.

* * * * *

Dedication 3,998,963.—*John A. Durden, Jr.*, South Charleston, and *Anthony A. Sousa*, Saint Albans, W. Va. TERTIARY BUTYL SUBSTITUTED CARBAMOYL OXIME PESTICIDES. Patent dated Dec. 21, 1976. Dedication filed Mar. 30, 1977, by the assignee, *Union Carbide Corporation.*

Hereby dedicates to the Public the remaining term of said patent.

[*Official Gazette May 24, 1977.*]